(12) United States Patent
Maillefer et al.

(10) Patent No.: US 9,795,960 B2
(45) Date of Patent: Oct. 24, 2017

(54) DEVICE AND METHOD FOR DRIED FLUID SPOT ANALYSIS

(71) Applicant: DBS SYSTEM SA, Gland (CH)

(72) Inventors: Didier Maillefer, Lausanne (CH); Julien Deglon, Gland (CH); Aurelien Thomas, Montreal (CA); Julien Dumont, Carouge (CH)

(73) Assignee: DBS SYSTEM SA, Gland (CH)

( * ) Notice: Subject to any disclaimer, the term of this patent is extended or adjusted under 35 U.S.C. 154(b) by 340 days.

(21) Appl. No.: 14/388,329

(22) PCT Filed: Mar. 7, 2013

(86) PCT No.: PCT/IB2013/051802
§ 371 (c)(1),
(2) Date: Sep. 26, 2014

(87) PCT Pub. No.: WO2013/144743
PCT Pub. Date: Oct. 3, 2013

(65) Prior Publication Data
US 2015/0037903 A1    Feb. 5, 2015

(30) Foreign Application Priority Data

Mar. 31, 2012   (WO) .................. PCT/IB2012/051578

(51) Int. Cl.
*B01L 3/00* (2006.01)
*G01N 33/49* (2006.01)

(52) U.S. Cl.
CPC ......... *B01L 3/5023* (2013.01); *B01L 3/50273* (2013.01); *B01L 3/502753* (2013.01);
(Continued)

(58) Field of Classification Search
CPC .................................................... B01L 3/5023
(Continued)

(56) References Cited

U.S. PATENT DOCUMENTS

| 5,620,097 A * | 4/1997 | Timmons, II | A61B 10/0096 |
| | | | 206/456 |
| 2004/0018117 A1* | 1/2004 | Desmond | B01L 3/502746 |
| | | | 422/64 |

(Continued)

FOREIGN PATENT DOCUMENTS

| EP | 2420831 A1 | 2/2012 |
| WO | WO 99/57559 A1 | 11/1999 |

OTHER PUBLICATIONS

Kazuo Hosokawa, Masaki Omata, Kae Sato and Mizuo Maeda "Power-free sequential injection for microchip immunoassay toward point-of-care testing" Lab Chip, 2006, 6, 236-241.*

(Continued)

*Primary Examiner* — Christine T Mui
*Assistant Examiner* — Emily Berkeley
(74) *Attorney, Agent, or Firm* — Sheridan Ross P.C.

(57) ABSTRACT

A lab-on-chip-based system is described for the direct and multiple sampling, control of the volume, fluid filtration, biochemical reactions, sample transfer, and dried spot generation on the conventional and commercial cards for dried fluid spot. Within an all-in-one integrated holder, the invention allows the complete process required to ensure a quantitative analysis of blood, plasma or any other fluids, modification and enrichment of molecule subsets, and formation of a dried fluid spot on the specific spot location of a passive cellulose, non-cellulose, absorbent, or non-absorbent membrane material sampling.

19 Claims, 1 Drawing Sheet

(52) U.S. Cl.
CPC .... *G01N 33/491* (2013.01); *B01L 2300/0609* (2013.01); *B01L 2300/0681* (2013.01); *B01L 2300/0816* (2013.01); *B01L 2300/123* (2013.01); *B01L 2400/0406* (2013.01); *Y10T 436/255* (2015.01); *Y10T 436/2575* (2015.01)

(58) Field of Classification Search
USPC ........................................................ 436/178
See application file for complete search history.

(56) References Cited

U.S. PATENT DOCUMENTS

2008/0286150 A1    11/2008  Pankow
2011/0086434 A1*    4/2011  Shin .................. B01L 3/502738
                                                            436/501
2012/0018629 A1     1/2012  Eikel et al.

OTHER PUBLICATIONS

International Search Report prepared by the European Patent Office on Jul. 15, 2013, for International Application No. PCT/IB2013/051802.
Written Opinion prepared by the European Patent Office on Jul. 15, 2013, for International Application No. PCT/IB2013/051802.

* cited by examiner

DEVICE AND METHOD FOR DRIED FLUID SPOT ANALYSIS

CROSS REFERENCE TO RELATED APPLICATIONS

This application is a national stage application under 35 U.S.C. 371 and claims the benefit of PCT Application No. PCT/IB2013/051802 having an international filing date of Mar. 7, 2013, which designated the United States, which PCT application claimed the benefit of International Application No. PCT/IB2012/051578 filed Mar. 31, 2012, the disclosure of each of which are incorporated herein by reference.

FIELD OF INVENTION

The present invention relates to a device and a method for collecting, treating and analyzing biological samples. It more precisely relates to dried fluid spot analysis, for instance dried blood spot (DBS) analysis.

STATE OF THE ART

Over the past decade DBS analysis has enjoyed growing popularity as an alternative sampling procedure in the bioanalytical, clinical and pharmaceutical community. Indeed, DBS offers numerous advantages over conventional whole blood, plasma, or serum sample collection. Furthermore, the procedure is clearly less invasive and cost effective in terms of sample collection, shipment and storage. Due to its easiness, the DBS collection can be performed after a small finger prick in a non-hospital environment with minimal training by technicians or even by patients themselves. Furthermore, the DBS sample process does not require the use of anticoagulant or plasma separation and ensures better stability of the compounds during shipment and storage without refrigeration. Lastly, the DBS process reduces the risk of infection by pathogens such as HIV or hepatitis, to a minimum. Since its introduction for phenylketonurea screening in newborns, DBS sampling form has been successfully applied to multiple neonatal metabolic disorder screening programs, and more recently to the monitoring of therapeutic agents, pharmacokinetic, and toxicokinetic studies. These combined advantages make the DBS procedure a patient-friendly tool for blood collection, especially in problematic and vulnerable patient populations. The ease of the process can also help in the recruitment of subjects (human and animal) for preclinical and clinical studies.

State-of-the-art DBS analysis however shows some disadvantages. Filter paper is a passive support for blood collection. Direct plasma analysis or accurate volume measurements for quantitative analysis require off-line manipulations that are time and cost-consuming for the user.

U.S. Pat. No. 6,036,659 (Ray et al.) discloses a device used in the analysis of a biological component in a dried blood or urine sample obtained from a living organism for collection, transport, storage, processing (e.g., separation of cells from serum), and compatibility with laboratory analysis of a biological sample. This device is particularly adapted for collection of a whole blood sample, allowing separation of the blood cells from the blood serum or plasma, drying the blood serum or plasma sample on the device, transporting the collected and dried blood serum or plasma sample to a laboratory or other facility for analysis, and extracting an analyte of interest from the sample for determining presence or absence of the analyte or, if present, the concentration thereof.

Although very interesting, this device however shows some disadvantages. It is for instance not possible to carry out on the same device several samplings or biochemical transformations of analytes contained in the fluid. This device is furthermore not compatible with the most conventional dried-spot sampling cards, including #903® brand paper (Whatman, Inc., New Jersey USA) or treated filter papers, such as FTA and FTA Elute brand paper (Whatman, Inc., New Jersey USA).

GENERAL DESCRIPTION OF THE INVENTION

The present invention offers several improvements with respect to the state of the art.

It relates to a device and a method for using said device as defined in the claims.

Among other features, the invention allows the use of conventional dried-spot sampling cards that may incorporate cellulose and/or non-cellulose storage media. The invention provides a lab-on-chip-based solution for the direct and multiple sampling, control of the volume, fluid filtration, biochemical reactions, sample transfer, and dried spot generation on the conventional and commercial cards for dried fluid spot. Within an all-in-one integrated holder, it allows the complete process required to ensure a quantitative analysis of blood, plasma or any other fluids based on cellulose, non-cellulose, absorbent, or non-absorbent membrane material sampling. As example, the invention can support the most conventional dried spot sampling supports including #903® brand paper (Whatman, Inc., New Jersey USA), bond elut dried matrix spotting (Agilent, Germany) or treated filter papers, such as FTA and FTA Elute brand paper or DMPK A, B or C card (Whatman, Inc., New Jersey USA).

The device according to the invention comprises a card holding element including at least the following features:
- an open cavity located on a face of said card holding element and defined by a bottom surface surrounded by a spacer,
- a fluid channel sized in a way as to induce a capillary action and defined by an outlet located in said bottom surface and an inlet located on another face of said card holding element, said spacer being adapted to support and hold a sampling card which, when present, covers said cavity.

In one preferred embodiment of the invention the card holding element comprises several fluid channels.

In another embodiment, the device comprises a lid, which is adapted to be fixed to the spacer, for instance by clipping. The lid, when fixed to the spacer, being furthermore designed to bring the flexible card into contact with the outlet.

DETAILED DESCRIPTION OF THE INVENTION

The invention will be better understood below, in particular with non-limiting examples illustrated by the following figures.

Figure 1:
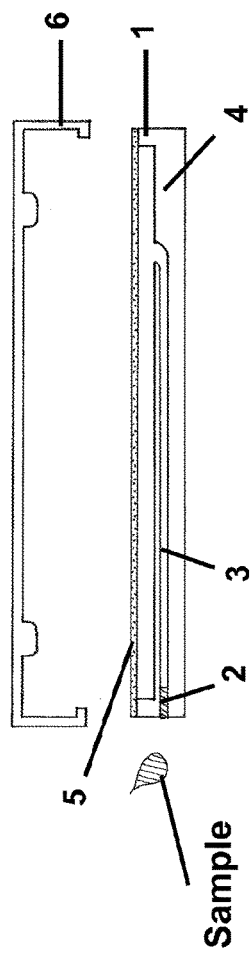
FIG. 1 shows a first embodiment (cross section, side view) of the device according to the invention comprising a card holding element with a lid, in a phase where the lid is not fixed to the card holding element.

As shown in the figures, a flexible conventional or non-conventional sampling card 5 is fixed to a card holding element 4 which includes a cavity defined by a bottom surface surrounded by at least one spacer 1 which maintains the storage card above the bottom surface (see FIG. 1). The card holding element 4 contains at least one fluid channel 3 (see also FIG. 2) defined between an outlet 7 located in the bottom surface and an inlet 2 located in another face of the card holding element 4. Advantageously the card holding element 4 contains several fluid channels 3 which are set in-line to allow multiple and independent samplings according to the number of spot locations 8, around said outlets 7. Each channel 3 is designed to produce a dried fluid spot within those spots 8. The channels 3 may have different geometries. They may have a linear or a curved shape. Preferably the channel section, length and material are chosen in a way as to induce a capillary effect, i.e. a driving force, to the fluid sample, which is entering the channel 3.

Figure 2:
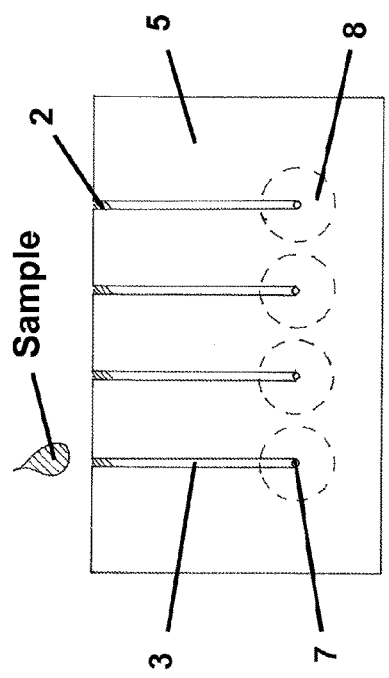
FIG. 2 shows another embodiment of the invention with a card holding element including several fluid channels.

In operation, a fluid to analyze is brought into contact with the inlet(s) 2 (see FIGS. 1 and 2). At least one drop of the fluid is then traveling mechanically or by capillarity through the channel 3. It should be underlined that any suitable element, e.g. mechanical, can be added to the device for facilitating and/or increasing the fluid motion through the inlet filter membrane 2 or along the channel 3. Usual traveling time through the channel(s) takes a few seconds. Advantageously the inlet 2 is provided with a filter membrane that, for instance, may filtrate the fluid and separate red cells from the blood. Interestingly, enzymes, antibodies or chemicals can be blotted on this membrane to treat the biological fluid before its transfer toward the channel 3.

The channel 3 is advantageously calibrated to accept a predetermined volume of fluid (typically 5-50 μL). This volume can be modified according to the required analysis. Furthermore, the channel 3 may incorporate different in-situ functionalization to provide specific biochemical properties. In this way, chemical, antibody, or enzyme blotting may be introduced into the channel 3 for providing analyte target enrichment and/or modification. As example, enzyme, like cytochrome P450 or trypsin can be introduced to ensure phase I drug metabolism and protein digestion, respectively.

Simultaneously, the channel 3 may also be used for the separation of molecules of interest according to their hydrophobic, hydrophilic, anion and cation exchange, metal and immune affinities as example. Several dimensions of chemical properties can also be assigned to different sections of a same channel 3 for serially enriched molecule subset according to different chemical properties. Fractionation of the channel 3 can provide the possibility of combining sequential analyte treatments. A first portion can assume the enrichment process for a specific target or subclass of analytes whereas a second can induce the biochemical or chemical modification of this analyte subset.

In another configuration, these different sample pretreatments may be independently carried out on each channel 3. In this manner the same fluid drop can be brought to multiple dried spots 8 having each a different molecular signature (FIG. 2). This feature is particularly interesting associated to clinical research by allowing the possibility of increasing the selectivity and the sensitivity of the analysis. When it has reached the outlet 7, the fluid preferably forms a static dome shaped object. Such an object results from the predefined calibrated volume of fluid and the capillary forces at the outlet 7.

Figure 3:
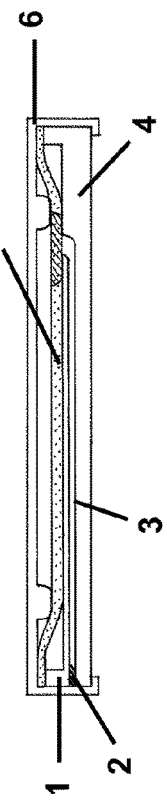
FIG. 3 shows the same embodiment of FIG. 1 but with the lid fixed to the card holding element.

The flexible card 5 is then forced towards the outlet 7, either by directly pushing the card 5 with the fingers or via a lid 6 (see FIGS. 1 and 3) which could be clipped to the card holding element 4.

Any other suitable pushing means can be used for bringing the card 5 into contact with the outlet 7. For instance, a strip attached to the holding element 4 can be used to manually slide the holding element 4 along the lid 6. This operation allows the lid 6 to be brought in front of the lip, which ensure the contact between the card 5 and the fluid at the outlet 7.

The contact between the card 5 and the fluid at the outlet 7 generates a dried fluid spot on the card 5. Advantageously the outlet 7 may form a right angle with an aperture oriented toward the card 5. As mentioned previously the lid 6 may be replaced by another pushing means such as a finger. However, it offers a protection for the sample particularly for shipment of the paper card to the laboratory.

What is claimed is:

1. A dried spot fluid sampling device, comprising:
    a card holding element including an open cavity located on a face of the card holding element and defined by a bottom surface surrounded by a spacer, and
    a fluid channel defined between an outlet located in the bottom surface and an inlet located on another face of the card holding element, a dried fluid spot to be formed at the outlet, the channel configured to induce a capillary action on a fluid moving within the channel towards a location of the dried fluid spot,
    the spacer configured to support and hold a sampling card which, when arranged on top of the spacer, covers the cavity.

2. The device according to claim 1, wherein the card holding element comprises several fluid channels.

3. The device according to claim 1, further comprising:
    a lid configured to be fixed to the spacer,
    wherein the lid, when fixed to the spacer being further configured to bring the card into contact with the outlet.

4. The device according to claim 1, wherein the inlet is provided with a filter.

5. The device according to claim 1, wherein the channel is biochemically functionalized.

6. The device according to claim 5, wherein the card holding element further comprises several channels which are biochemically functionalized in a different manner from each other.

7. The device according to claim 1, wherein the card is flexible.

8. A method for using a device as defined in claim 1 and comprising the following successive steps:
    fixing a card on the spacer,
    bringing a predefined volume of a fluid to collect into contact with the inlet,
    waiting until the fluid has reached the outlet,
    forcing the card onto the outlet in such a way as to obtain a dried fluid spot on the card.

9. The method according to claim 8, wherein the card is forced onto the outlet with a lid.

10. The method according to claim 8, wherein the channels are fractionated to serially combine different sample/molecule enrichments, separations and transformations.

11. The device according to claim 3, wherein the lid comprises a clipping mechanism to secure the lid to the spacer.

12. The device according to claim 4, wherein the fluid includes blood, and the filter is configured to separate red cells from the blood.

13. A system for dried spot fluid sampling, comprising:
a dried spot sampling card; and
a card holding element,
wherein the card holding element includes,
- an opening exposing a bottom surface, the opening surrounded by a spacer, the spacer configured to removably hold the dried spot sampling card, and
- a fluid channel having an inlet at a side wall of the card holding element and an outlet for forming a dried fluid spot when the outlet is brought into contact with the dried spot sampling card, the fluid channel configured to induce a capillary action on a fluid moving within the channel towards the outlet.

14. The device according to claim 1, wherein the outlet is configured to form the dried fluid spot on the sampling card.

15. The system according to claim 13, wherein the outlet is formed on the bottom surface of the card holding element.

16. A dried spot fluid sampling device, comprising:
a card holding element, comprising:
- a first surface and a second surface parallel to and spaced from the first surface, and at least one side wall extending between the perimeter of the first and second surfaces;
- at least one fluid channel having an inlet and an outlet spaced from the inlet, the inlet located in the side wall and the outlet located in the first surface interior of the side wall, and wherein the at least one fluid channel is configured to induce a capillary action on a fluid moving within the channel towards the outlet; and
- a spacer extending outwardly from the first surface and surrounding the outlet, the spacer configured to removably hold a dried spot sampling card;

wherein when a fluid is introduced to the inlet of the at least one channel and the dried spot sampling card is brought in contact with the outlet of the at least one channel, a fluid spot is formed on the dried spot sampling card.

17. The device according to claim 16, further comprising:
a lid configured to be fixed to the spacer,
wherein the lid, when fixed to the spacer being further configured to bring the card into contact with the outlet.

18. The device according to claim 16, wherein the channel is biochemically functionalized.

19. The device according to claim 16, wherein the inlet is provided with a filter.

* * * * *